(12) United States Patent
Bauer

(10) Patent No.: US 11,166,820 B2
(45) Date of Patent: Nov. 9, 2021

(54) POROUS STRUCTURE FOR BONE IMPLANTS

(71) Applicant: WALDEMAR LINK GmbH & Co. KG, Hamburg (DE)

(72) Inventor: Eckhard Bauer, Kiel (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 378 days.

(21) Appl. No.: 15/742,704

(22) PCT Filed: Jun. 24, 2016

(86) PCT No.: PCT/EP2016/064731
§ 371 (c)(1),
(2) Date: Jan. 8, 2018

(87) PCT Pub. No.: WO2017/005514
PCT Pub. Date: Jan. 12, 2017

(65) Prior Publication Data
US 2018/0193152 A1    Jul. 12, 2018

(30) Foreign Application Priority Data
Jul. 9, 2015  (EP) .................................... 15176117

(51) Int. Cl.
A61F 2/30    (2006.01)
A61F 2/34    (2006.01)
(Continued)

(52) U.S. Cl.
CPC ...... *A61F 2/30734* (2013.01); *A61F 2/30771* (2013.01); *A61F 2/34* (2013.01);
(Continued)

(58) Field of Classification Search
CPC .......................... B22F 3/1055; A61F 2/30734
See application file for complete search history.

(56) References Cited

U.S. PATENT DOCUMENTS

| | | |
|---|---|---|
| 5,433,750 A | 7/1995 | Gradinger et al. |
| 8,344,042 B2 | 1/2013 | Liu et al. |

(Continued)

FOREIGN PATENT DOCUMENTS

| | | |
|---|---|---|
| DE | 10 2012 213 246 | 1/2014 |
| EP | 0 561 263 | 9/1993 |

(Continued)

OTHER PUBLICATIONS

Search Report dated Oct. 5, 2018, directed to Russian Application No. 2018104870; 4 pages.

(Continued)

*Primary Examiner* — Olivia C Chang
(74) *Attorney, Agent, or Firm* — Joseph V. Saphia; Haug Partners LLP

(57) ABSTRACT

A bone implant includes a body having a porous structure and having a size and shape configured for fitting to a bone, preferably in a bone defect. The porous structure is comprised of regularly arranged elementary cells whose interior spaces form interconnected pores, the elementary cells are formed by basic elements arranged in layers, wherein the basic elements are shaped like tetrapods, the tetrapods in each layer being arranged in parallel orientation and being positioned in-layer rotated with respect to tetrapods of an adjacent layer. The layers with rotated and non-rotated tetrapods are alternatingly arranged. Thereby a porous structure can be achieved which features improved mechanical characteristics, leading to improved biocompatibility.

37 Claims, 5 Drawing Sheets

(51) Int. Cl.
  *A61F 2/44*     (2006.01)
  *B33Y 80/00*    (2015.01)
  *B22F 5/10*     (2006.01)
  *B22F 10/20*    (2021.01)
  *A61F 2/38*     (2006.01)
  *A61F 2/40*     (2006.01)
  *B22F 7/00*     (2006.01)

(52) U.S. Cl.
  CPC ............ *A61F 2/389* (2013.01); *A61F 2/3859* (2013.01); *A61F 2/4081* (2013.01); *A61F 2/447* (2013.01); *B22F 5/10* (2013.01); *B22F 10/20* (2021.01); *B33Y 80/00* (2014.12); *A61F 2/3094* (2013.01); *A61F 2002/30011* (2013.01); *A61F 2002/3092* (2013.01); *A61F 2002/3097* (2013.01); *A61F 2002/30303* (2013.01); *A61F 2002/30449* (2013.01); *A61F 2002/30578* (2013.01); *A61F 2002/30736* (2013.01); *A61F 2002/30738* (2013.01); *A61F 2002/30769* (2013.01); *A61F 2002/30914* (2013.01); *A61F 2002/30915* (2013.01); *A61F 2002/30971* (2013.01); *A61F 2310/00011* (2013.01); *A61F 2310/00017* (2013.01); *A61F 2310/00023* (2013.01); *A61F 2310/00029* (2013.01); *A61F 2310/00089* (2013.01); *A61F 2310/00131* (2013.01); *A61F 2310/00485* (2013.01); *A61F 2310/00491* (2013.01); *A61F 2310/00544* (2013.01); *A61F 2310/00796* (2013.01); *B22F 7/002* (2013.01); *B22F 7/004* (2013.01); *B22F 2999/00* (2013.01); *Y02P 10/25* (2015.11)

(56) References Cited

U.S. PATENT DOCUMENTS

| | | | |
|---|---|---|---|
| 2006/0147332 A1* | 7/2006 | Jones | B23K 26/082 419/8 |
| 2010/0191345 A1 | 7/2010 | Pressacco et al. | |
| 2011/0166672 A1 | 7/2011 | Tei et al. | |
| 2012/0232654 A1 | 9/2012 | Sharp et al. | |

FOREIGN PATENT DOCUMENTS

| | | |
|---|---|---|
| EP | 0 709 070 | 5/1996 |
| EP | 1 683 593 | 7/2006 |
| RU | 2385740 | 4/2010 |
| WO | WO-97/38649 | 10/1997 |
| WO | WO-2013/006778 | 1/2013 |

OTHER PUBLICATIONS

International Search Report and Written Opinion dated Sep. 28, 2016, directed to PCT/EP2016/064731; 12 pages.

\* cited by examiner a)
b)

a)

b)

a)

b)

c)

POROUS STRUCTURE FOR BONE IMPLANTS

CROSS-REFERENCE TO RELATED APPLICATIONS

This application is a U.S. national phase patent application of International Patent Application No. PCT/EP2016/064731, filed Jun. 24, 2016, which claims priority to European Application No. 15176117.8, filed Jul. 9, 2015, each of which is hereby incorporated by reference in the present disclosure in its entirety.

FIELD OF THE INVENTION

The invention relates to an implantable bone augment made of porous material. The invention further relates to a manufacturing method for said implantable bone augments.

BACKGROUND OF THE INVENTION

In surgery, in particular for implanting artificial joints, the issue of bone defects is a scenario which is encountered quite often. The defects are to be filled in order to give back the defect bone its original shape and size. Autografted material or allografted material may be employed for this purpose. Artificially made allografted material has an advantage in terms of ease of use and reproducibility. Further, synthetically made material have the advantage of being subject to tighter quality control and being free of any risk of diseases.

Prosthetic elements and bone implants are known having a lattice like porous structure. The porous structure preferably possesses a regular geometry with the aim to promote biologic fixation to surrounding bony tissue. The porous material is configured such as to encourage ingrowth of surrounding bone into the pore spaces of the porous material. Typically, the porous material and/or any coating applied to may comprise titanium alloys, pure titanium, cobalt chromium, stainless steel, tantalum, zirconium and other biocompatible materials. Such augments are commercially available in different shapes and sizes. Particularly, augments made of metallic foam material having a high degree of porosity are manufactured and sold by Zimmer Inc. (Trabecular Metal®).

It is known to create a porous structure by additive methods like Selective Laser Melting (SLM) or Electron Beam Melting (EBM). These methods allow to make products in component of metal material with a process building layers of solidifying material from powder by means of a melting process. Thereby with great precision a wide range of desired structures may be formed. It is for example known to attach a porous structure to a cup of an acetabula endoprosthesis (U.S. Pat. No. 8,454,705 B2). The porous structure is obtained by EBM and forms a lattice having a regular arrangement of open cells. The cells are configured in a diamond-like configuration which provide a priority of the geometrical measures of a hexagonal shape in various planes. The terms "diamond" or "diamond-like" in the context of this patent relates to a cubic crystal structure which is a face-centered cubic Bravais lattice. The diamond structure with its hexagonal shape has the advantage of rather high stiffness. However, combined with a rather strong biocompatible materials the resulting overall stiffness may be rather high.

SUMMARY OF THE INVENTION

According to some embodiments, a porous structure for an implant provides an improvement in terms of load bearing characteristics.

According to some embodiments, a bone implant comprises a body having a porous structure and having a size and shape configured for fitment to a bone, preferably in a bone defect, wherein the porous structure is comprised of regularly arranged elementary cells whose interior spaces form interconnected pores, wherein the elementary cells are formed by basic elements arranged in layers, wherein the basic elements are shaped like tetrapods, the tetrapods in each layer being arranged in parallel orientation and being positioned in their layer rotated with respect to the tetrapods of an adjacent layer.

Some terms may be explained beforehand:

A "tetrapod" is known to the person skilled in the art as being an element having four legs emanating from a common center pointing in four different directions such that the legs with their free ends span a tetrahedron. In many cases the legs will have an identical or similar length, although this is not a must. Having legs of different length yields the advantage that it produces different angles between the legs. With all legs having the same length the angle between them would be always the same, namely a so called Tetraeder angle which is defined as being arccos $(-\frac{1}{3})$, or approximately 109.47°. With legs of different length, different angles result, so that some of these angles will be smaller than the Tetraeder angle, and preferable even be smaller than 100°. Surprisingly it was found that having such small angles in the elements which define the structure of the elementary cells provides an improved ingrowth of bony tissue, which is a huge advantage for the inventive augment device.

A contacting surface is a surface of the implantable bone augment which is configured to be brought in contact with a surface of the bone in an implanted state of the bone augment.

A node point is point in which different elements interconnect, in particular a point where one tetrapod connects with a far end of one of its legs to at least one far end of one of the legs of another tetrapod.

An offset relation between layers means that the layers concerned are shifted in respect to each other along a plane defined by the layers. The shifting can be translational, rotational or both.

The term "adjacent" layer means the directly neighbouring layer.

An extended centerline is an imaginary line along a median of an elongated element, in particular a leg of the tetrapods, which extends beyond the physical limits of said elongated element.

The term "directly underneath" means along an extended centerline of the fourth leg of a tetrapod, the center line being extended beyond that tetrapod's center.

At the core of the invention is the concept of arranging the elementary cells in different layers, wherein the elementary cells are formed by inter-connected tetrapods, wherein the layers are alternating shifted such that the tetrapods of one layer are rotated in respect to its adjacent lower layer.

Surprisingly, the porous structure having this configuration features improved mechanical characteristics, wherein Young's modulus in one direction in space is different from Young's modulus in another direction. Having such different Young's moduli in different direction is a huge advantage in biocompatibility. This is since stiffness of natural bone is usually direction dependent, particularly with respect to large load carrying bones, like the femur and tibia of the human leg (and correspondingly humerus and fibula of the human leg) and the acetabulum for the hips. The advantage of the microstructure according to the present invention becomes prominent if contrasted to another microstructure for bone augments, namely having elementary cells formed in diamond-like lattice. Although such a diamond-like structure has good load carrying capability owing to its high Young's modulus, it shows the same high Young's modulus in all cardinal directions. This is a disadvantage in terms of biocompatibility in particular with respect to bone augments, since natural bone—as already stated above—shows different stiffness in different directions. The invention overcomes this disadvantage, even more so in a preferred embodiment, configuring the offset such that a node point of the adjacent lower layer is located underneath the top leg of the tetrapods of the adjacent upper layer such that an extended centerline of the top leg runs through the node point. Thereby the load bearing capability is further improved only in the direction of the extended centerline which is perpendicular to the plane of the layers.

Briefly stated, the claimed shifted arrangement of the layers which are otherwise regularly arranged tetrapods provides an unexpected huge improvement in biocompatibility.

Preferably the rotation is in-plane, i.e. with an axis of rotation being perpendicular to the plane defined by the layer.

The elementary cells within either layer define an interior space within each elementary cell, and this interior space is—by virtue of the offset inter-layer relation—unsymmetrical in the three dimensions of space. The three dimensions of space are the cardinal directions of an orthonormal system, wherein one of the directions coincides with the direction of the top leg of the tetrapods defining the elementary cell.

In other words the claimed configuration provides a porous structure which is considerably different from the known diamond configuration. According to the claimed relative rotation between the tetrapods of one layer to that of the direct next layer, a new kind of elementary cell is provided by the invention which is nearly as compact as the diamond elementary cell but has the advantage that stiffness is not uniform in all three direction of space, rather it varies depending on the direction. Since natural bone, in particular a *Spongiosa* section of the bone is showing different stiffness depending on direction of load, the porous structure provided by the invention demonstrates a similar characteristic and therefore achieves a higher degree of biocompatibility. This is a rather high advantage since bone material tends to degenerate if it is adjacent to an implant which has a different stiffness. By adapting the stiffness to the characteristic directional variation of natural bone, this unwanted degradation could be avoided. This is a major benefit of implants having the claimed inventive porous structure.

Preferably, the claimed rotated position relates to a true rotation by an angle leading to an oblique position—a rotation by 360° or multiples thereof and 180° or multiplies are not considered rotations as they relate to the trivial case of non-rotation or just inversion.

Preferably within each layer three adjacent tetrapods connect with each other with one of their legs in a node point, and the node points define a base plane of said layer, and a fourth leg of said tetrapods is oriented essentially perpendicular to the base plane. By virtue of this, a well-defined lateral offset is achieved between the tetrapods of two adjacent layers. For any load being put on the porous structure in the direction of the fourth leg a higher stiffness will be achieved than in any of the other directions. Further preferably, the node points of said layer are positioned directly underneath the fourth legs of the tetrapods of an adjacent upper layer. The aforementioned effect can be further increased by selecting the offset between layers such that the fourth leg of a tetrapod of the adjacent upper layer aims directly to the node point of three adjacent tetrapods of the adjacent lower layer. As indicated by the term "aims" said fourth leg points to the node point of the adjacent lower layer but is still spaced apart from it, i. e. said fourth leg does not actually contact the node point of the adjacent lower layer.

In a preferred configuration the legs of the tetrapods are oriented essentially perpendicular or oblique but not parallel to the base plane. By avoiding tetrapods having legs being oriented parallel to the base plane manufacturing of the porous structure with additive manufacturing methods, like Electron Beam Melting (EBM) or Selective Laser Melting (SLM) is much facilitated. More rational production can be even achieved by forming the tetrapods in place by depositing and solidifying, preferably in successive layers. This can be achieved by the aforementioned EBM and SLM process.

In the context of the present patent a standard orientation of the tetrapod shall be one of the legs pointing upwards ("top leg") and the other three legs forming a stand ("base legs"), wherein the far ends of the three base legs define a base plane. Preferably an angle between each of the base legs and the base plane is more than 20°, preferably it is in a range from 25° to 35°. By virtue of this a steeper arrangement of the base legs could be achieved, which allows a facilitated manufacturing, in particular by the methods described above. Preferably the three base legs are oriented equiangular from each other, thereby spanning an isosceles triangle.

It is further preferred to dimension the fourth leg of the tetrapod to be shorter than the base legs. This allows for a steeper arrangement of the base legs while maintaining the general shape of the tetrahedron spanned by the legs of the tetrapod. It is particularly preferred to select—depending on the angle of the base legs to the base plane—the top leg so short such that the free ends of the legs span a regular tetrahedron. Thereby the advantage of having a regular (i.e. ideal) tetrahedron is combined with a more robust configuration and manufacturing of the tetrapods, i.e. providing for a much improved practicability. Further, as already explained above, different angles result with some angles becoming smaller, which is beneficial for prompting ingrowth of bony tissue.

Preferably the layers are alternatingly shifted such that the tetrapods of one layer are rotated with respect to the tetrapods of the adjacent layer, preferably in an alternating arrangement of layers having rotated and non-rotated tetrapods. Such an alternating arrangement combines efficient manufacturing with the improved implant characteristics of the invention. It is to be noted that by such an alternating arrangement only two different types of layers are required, a first layer with the tetrapod in their original (non-rotated) state and a second layer with the tetrapods being rotated; the first and second layers are to be arranged alternating. This provides a regular structure giving the discussed benefits which is superior to the known diamond-like configuration.

A preferred material for the porous structure is generally a biocompatible material. It is preferably selected from a group comprising titanium alloys, pure titanium, cobalt chromium, tantalum, stainless steel, and zirconium. Further preferably, the material is Titanium Grade 2. This combines excellent biocompatibility with good strength and stiffness characteristics. Another preferred material is titanium alloy (e.g. Ti6Al4V). This material is more regularly available, also it has a slightly higher stiffness. Having such a biocompatible material for the elementary cells removes the need for a protective coating in order to achieve biocompatibility. However, this does not preclude the option of providing at least a portion of the elementary cells with a coating of bone growth promoting material, in particular calcium phosphate (CaP). Thereby, a more rapid and thorough ingrowth of adjacent natural bone material into the bone augment can be achieved. Further, the coating may be configured as being a PVD (Physical Vapour Deposition) coating. Its material is preferably selected from a group comprising niobium, tantalum, zirconium, and oxides thereof (niobiumoxide, tantalumoxide, and zirconiumoxide). Preferably, a thickness of the coating is selected to be between 1 μm and 10 μm, further preferable less than 7 μm. Thereby, even with such an additional coating a high degree of flexibility will be retained and rather wide interconnections of pores at the elementary cell level will still be achieved. Further, the combination of material and thinness provides for a coating that will be highly notch-resistant.

In a further preferred embodiment which may be eligible to independent protection the implantable bone augment further comprises a reinforcing structure, preferably made of a solid material. Thereby, robustness in terms of mechanical stress can be further increased, while maintaining the general advantages of the porous structure according to the invention. Preferably, the reinforcing structure is formed to be integral with the porous structure. Preferably the reinforcing structure comprises a solid body structure provided in addition to the porous structure, wherein the porous structure is attached to the solid body structure. Further preferably the solid body structure and the porous structure are formed as a unitary structure. Thereby more complex bone implants having additional functions, like cups for acetabula part of an implant, can be formed. It is particular preferable that the height and size of the bone implant is configured such as to be usable for an acetabular or humeral cup, or a bone augment device, preferably a femoral, tibial, acetabular or humeral augment.

According to a further aspect of the invention which may deserve independent protection, an endoprosthetic implant comprising a body made of a solid material and a bone contacting portion made of a porous structure is provided, wherein the porous structure is comprised of regularly arranged elementary cells whose interior spaces form interconnected pores, wherein the elementary cells are formed by basic elements arranged in layers, wherein the basic elements are shaped like tetrapods, the tetrapods in each layer being arranged in parallel orientation and being positioned rotated in their layer with respect to the tetrapods of an adjacent layer. In a preferred embodiment the body is a cup, preferably for an acetabulum part of a hip endoprosthesis. By virtue of the cup a proper bearing is formed for engaging a head of a femur part in an articulated manner. Owing to the combination with the porous structure according to the present invention a mechanical sound articulation is combined with an anchoring microstructure with improved biocompatibility, in particular in respect to stress loading and load transfer from the cup into the acetabulum. This applies mutatis mutandum to another preferred embodiment in which the body is a cup for a shoulder endoprosthesis.

In another embodiment, the body is a bulkhead element dividing the porous structure to distinct sections. Thereby it can be achieved that cement applied on one side of the body will not reach the other side of the bulkhead. In a further preferred embodiment, the body is a reinforcing element, and thereby providing additional mechanical strength.

Another preferred embodiment is of a cone-like shape having an interior channel running from a bottom to a top side and being configured such as to be enabled to accommodate a shank of an endoprosthesis, preferably a femur part of a hip endoprosthesis and/or femur and/or tibial parts of a knee endoprosthesis.

Yet another preferred embodiment is configured like a spinal cage. Spinal cages are implant devices which are to be placed in an intervertebral space between two adjacent vertebrae, in lieu of a natural vertebral disc which was removed or is defective. Thereby the spinal cages prevent a collapse of the intervertebral space. A long time goal of the spinal cage is to effect fusion of the two adjacent vertebrae by bone material growing in and into the intervertebral space. The spinal cage according to the instant embodiment features a porous inner core having the porous structure according to the present invention for promoting bone ingrowth. The inner core is surrounded by an encasement. It is made of solid material and serves a double purpose of carrying load forces and protecting the porous structure of the inner core. Further, on a top side and a bottom side of the encasement a plurality of arresting teeth are provided. They are pyramidal shaped for arresting the implant at its place. Further, they are slanted against direction of implantation, thereby facilitating implanting and blocking unwanted dislocation against the direction of implantation.

Preferably, the porous structure is dimensioned such that an average pore width is ranging between 0.1 and 1.5 mm, preferably between 0.4 and 1.0 mm, and the legs of the tetrapods defining walls of the pores having a thickness between 0.2 and 1.0 mm, preferably between 0.4 and 0.7 mm.

The invention further relates to a method for manufacturing a bone implant and comprises a body having a porous structure and having a size and shape configured for fitment to a bone, preferably in a bone defect, wherein the method comprises manufacturing the bone implant by using a deposition technique to form a porous structure, including forming alternating layers of basic elements which are shaped like tetrapods, arranging the tetrapods in each layer in essentially parallel orientation, rotating the tetrapods in every other layer with respect to the tetrapods of its proceeding layer, forming regularly arranged elementary cells whose interior spaces form interconnected pores, the elementary cells being defined by the basic elements arranged in layers. By virtue of this method the devices as detailed above can be manufactured. For further details a reference to the above explanations is made.

Preferably, the method further comprises the steps of providing a three-dimensional model of the bone implant, defining a body of the bone implant, defining a bone contacting surface of the bone implant which is configured to complement a corresponding surface of the bone, wherein at least the bone contacting surface is manufactured as a porous structure. Thereby a tailor made bone implant manufacture according to specific needs of a patient can be realized. Employing EBM or SLM process enables a precise and effective manufacturing of such implants.

Further preferably, the method is configured for manufacturing of a bone implant as claimed.

BRIEF DESCRIPTION OF THE DRAWINGS

In the following the invention will be described in more detail according to the combined drawing in an exemplary manner. In the drawings.

DETAILED DESCRIPTION OF THE INVENTION

Figure 1:
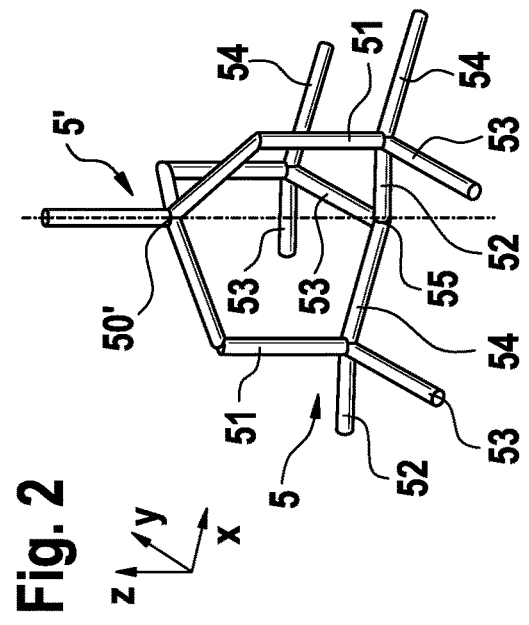
FIG. 1 is a detail view showing an elementary cell of a porous structure of a bone implant according to the invention.
Figure 2:
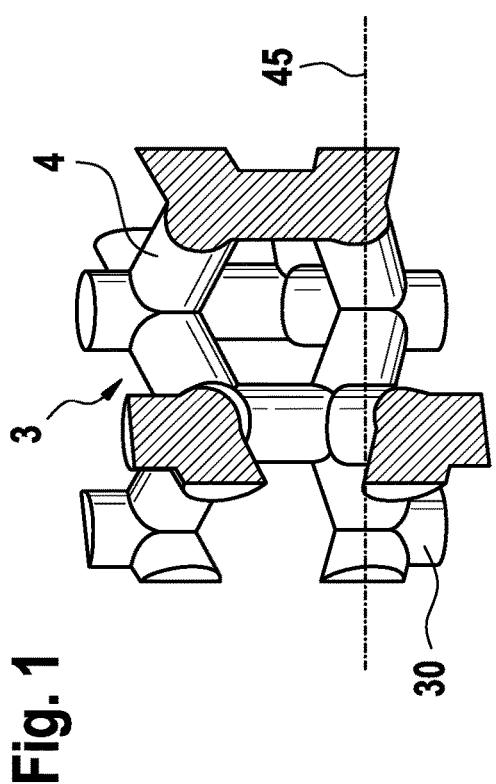
FIG. 2 is a schematic view of the elementary cell and tetrapods forming it.
Figure 3:
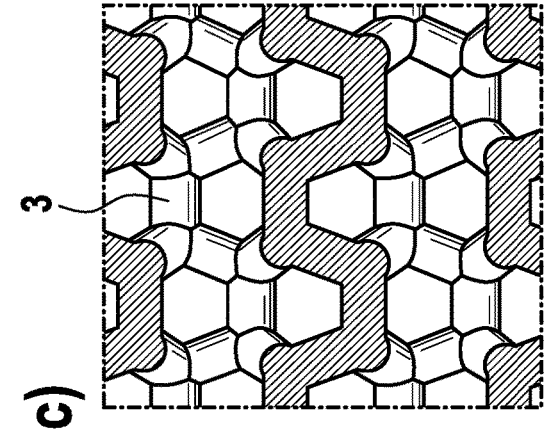
FIG. 3a-c are three views of the porous structure in the three directions of space.
Figure 3:
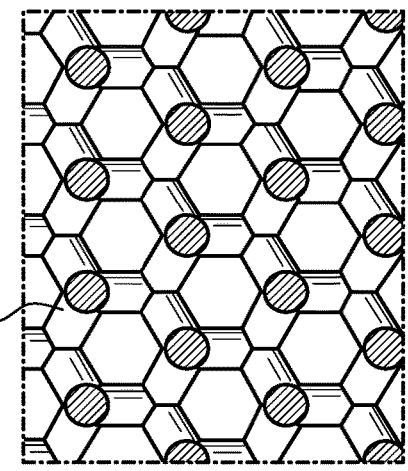
Figure 3:
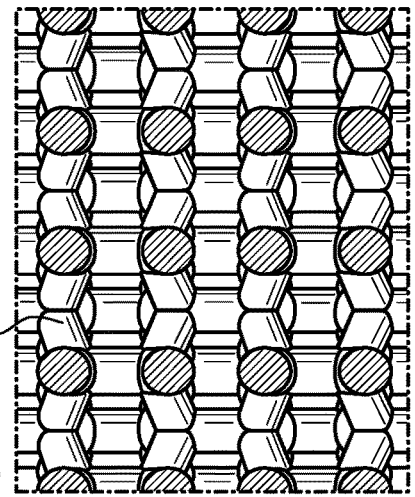

A porous structure to be used for various embodiments of endoprosthetic devices is shown in FIG. 1-3.

The porous structure 3 is comprised of regularly arranged elementary cells 4. A detail view of an elementary cell and its surroundings is shown in FIG. 1. The elementary cell features an internal free space 40 which is inter-connected with the internal free-space of neighboring elementary cells 4. The regular arrangement of the elementary cells 4 is shown in FIG. 2. As FIG. 3a-c show isometric views in all three dimensions of space (i. e. along an x, y, and z direction in a right-handed coordinate system) it can be appreciated that the elementary cells 4 are regularly arranged in layers, however details of arrangement differ between the directions as a mutual comparison of FIG. 2a-c shows. This is due to the peculiar configuration of the elementary cell 4, as will be explained in more detail in the following.

Each of the elementary cells 4 is formed by basic elements, wherein a basic element is shaped like a tetrapod 5. A tetrapod 5 is a structure having four legs 51, 52, 53, 54 being connected at a center point 50, each of the legs 51, 52, 53, 54 pointing away from the center point 50 and spanning with their free ends a tetrahedron.

The tetrahedron may be irregular or regular. Optionally an isosceles tetrahedron is formed wherein each of the legs 51, 52, 53, 54 would form the same angle α to each of the other three legs; in this case the angle α is defined to be $$\alpha = \arccos(-\frac{1}{3})$$

which is approximately 109.47°.

In the context of the present patent a standard orientation of the tetrapod shall be one of the legs 51, 52, 53, 54 pointing upwards ("top leg" 51) and the other three legs forming a stand ("base legs" 52, 53, 54), wherein the far ends of the three base legs 52, 53, 54 define a base plane 45.

For forming an elementary cell 4, three adjacent tetrapods 5 are connected with each other with one of their base legs 52, 53, 54 in a node point 55. A fourth tetrapod 5' is placed on top of the said three adjacent tetrapods 5 such that the free ends of its base legs 52', 53', 54' are connected to the free end of the top leg 51 of each of said three adjacent tetrapods 5. The space framed thereby is the internal space 40 of the elementary cell 4.

As can be appreciated best in FIG. 3, the fourth tetrapods 5' is arranged in a different, higher layer than the three tetrapods 5. Further, it can be readily appreciated that the fourth tetrapod 5' is positioned such that a projection of its top leg 51' beyond its center 50' runs straight through the node point 55 where the three tetrapods 5 of the adjacent, i.e. direct next lower layer are connected. In other words, the node point 55 is positioned such as to be directly underneath of the top leg of the fourth tetrapod in the adjacent, i.e. direct next upper layer.

Figure 13:
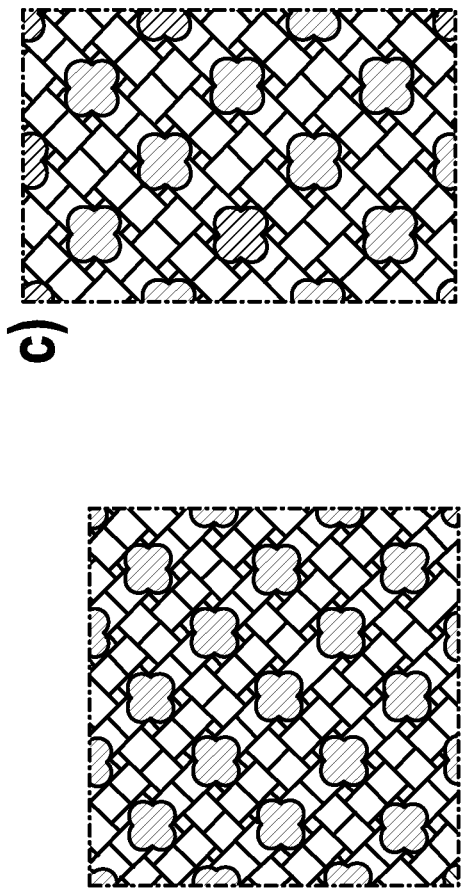
FIG. 13 is a schematic view of the known diamond elementary cell.
Figure 12:
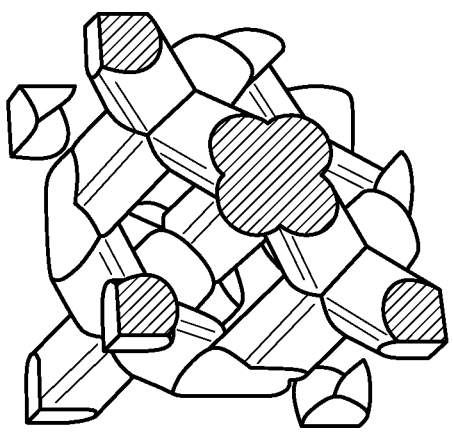
FIG. 12 is a detail view showing an elementary cell of a diamond-like porous structure as known in the prior art.
Figure 14:
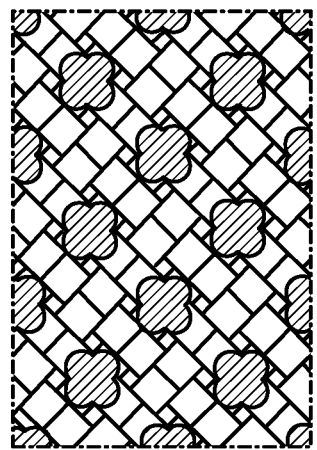
FIGS. 14a-c are three views of the diamond-like porous structure in the three directions of space.

This configuration of the elementary cell 4 is a peculiarity of the porous structure 3 of the present invention. The difference over the known diamond-like structure as shown in FIG. 12-14 is quite obvious. In the known diamond-like structure there is no such arrangement of the tetrapods. It lacks the essential feature of having the node point being positioned directly underneath the tetrapod of the adjacent upper layer (see FIG. 13). The resulting elementary cell is shown in FIG. 12. It is symmetric in all three dimensions, and as a result a stiffness of the porous structure is identical in all three directions of space, as shown in FIG. 14 a-c. Therein elements having same or similar functions are denoted by the same reference numerals as in FIG. 1-3.

Owing to this difference in structure the overall stiffness of the porous structure of the invention becomes direction-dependent and thus resembles more closely the characteristics of natural bone.

As a material for the porous structure preferable a titanium alloy or pure titanium is used.

The porous structure is formed by an Electron Beam Melting (EBM) process. This is an additive process for manufacturing and may produce solid or porous material. A powder of the desired material is provided in the desired granulometry. By the EBM process the powders of the desired material are deposited in successive layers at desired positions and in desired sequence (as defined in preceding modelling step for the porous structure) and made to melt such as to form a coherent body. Optionally, a coating 30 is provided on the porous structure by a Physical Vapor Deposition (PVD) process, preferably using tantalum; alternatively the coating 30 may be a calcium phosphate (CaP) coating.

Figure 4:
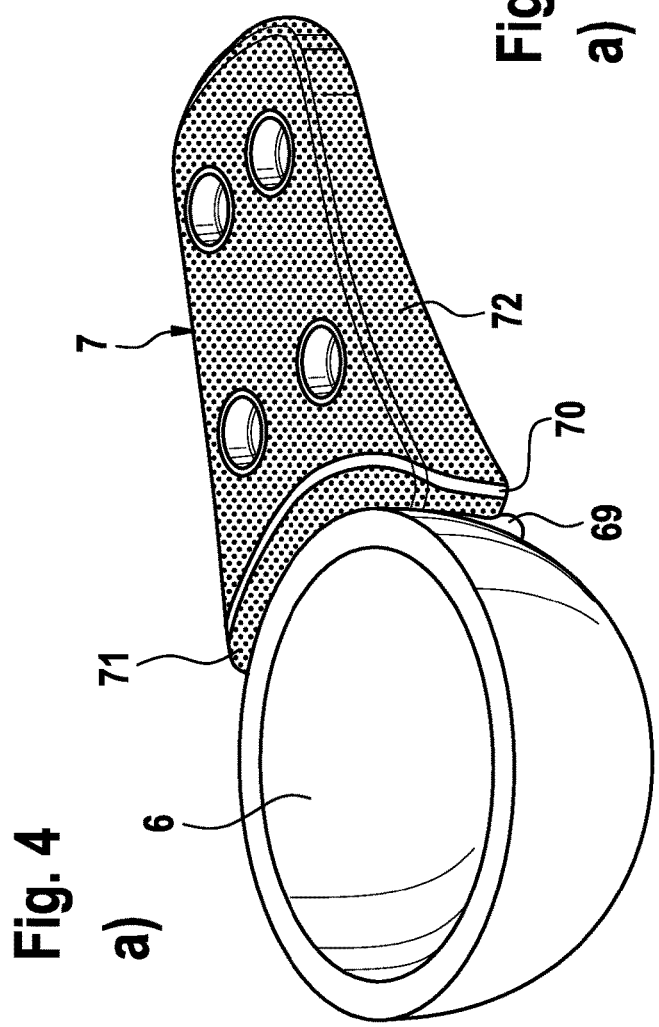
FIGS. 4a, b show a first embodiment of an endoprosthetic implant comprising a plate shaped augment device.

A first embodiment of a bone implant used for an endoprosthesis is shown in FIG. 4a, b. It comprises an acetabular cup 6 for the acetabular portion of hip endoprosthesis. The acetabular cup 6 is made of solid biocompatible material as known in the art. However, due to defects in the natural bone where the acetabular cup 6 is to be implanted, it may be necessary to provide a bone implant 7 for augmentation. The bone implant 7 is a plate shaped augment and it features a solid inner wall 70 and a first porous structure 71 on its inner and a second porous structure 72 on its outer side, the porous structure 71, 72 being configured as described above. The solid inner wall acts as a bulkhead isolating the porous structures 71, 72 from each other. Thereby, the porous structures 71, 72 can serve different purposes. The porous structure 71 may serve as a contacting surface to the acetabular cup 6. For affixing to the acetabular cup 6 cement 69 may be used, wherein the cement 61 enters the interconnected pores of the porous structure and as a result provides a strong fixation.

The porous structure 72 serves to fill bone defects. It may comprise passageways 73 covered with an internal lining 74 of solid material, which is manufactured using the same process at the same time as manufacturing the porous structure 72. Owing to the special configuration of the base elements 4 of the porous structure 72 according to the invention, the bone implant 7 has a rather high stiffness, thereby providing an improved load bearing capability in particular in the direction of increased stiffness. The porous structure 72 further encourages bone ingrowth, thereby enabling a reliable long-term fixation. For initial fixation attachments elements like bone screws (not shown) may be employed which are placed into the passageways 73. The internal lining 74 acts as a barrier to keep the passageways 73 free from any influx stemming from the porous portion which might interfere with bone screws and/or provide a load bearing support for a head of said bone screws.

Figure 5:
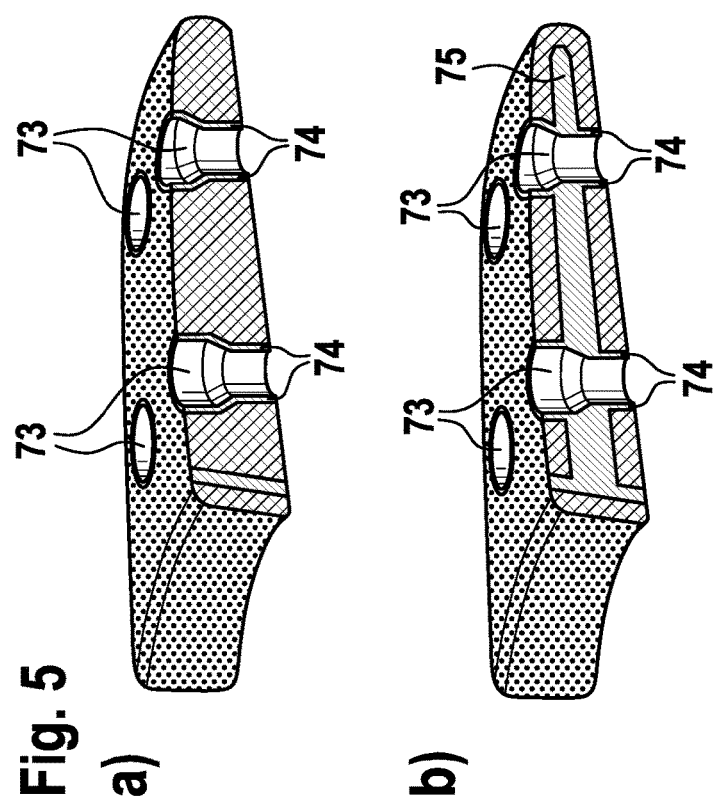
FIGS. 5a, b is a cross-section drawing of the plate shaped augment device and of a variant thereof.

In a variant shown in FIG. 5*b* a massive core portion 75 is provided within the porous structure 72. The core portion 75 acts as an additional reinforcement, in particular providing improved torsional resistance.

Figure 6:
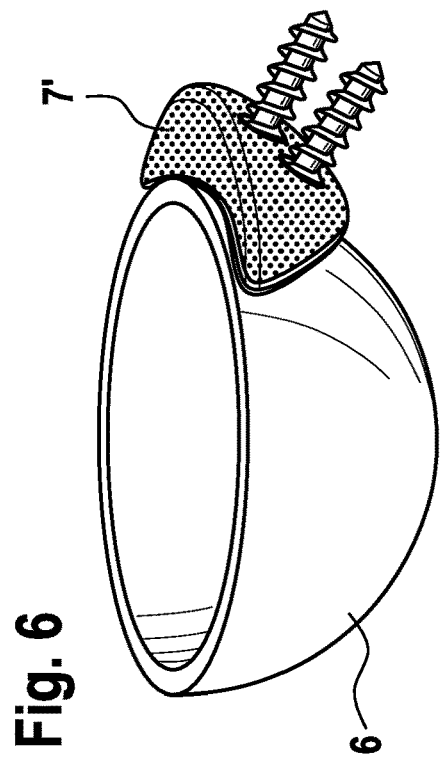
FIG. 6a shows a second embodiment of an endoprosthetic implant comprising a segmental augment device.
Figure 8:
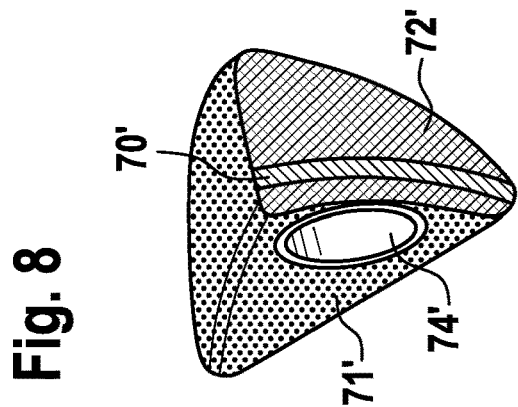
FIG. 8 is a cross-sections drawing of the segmental augment device.
Figure 7:
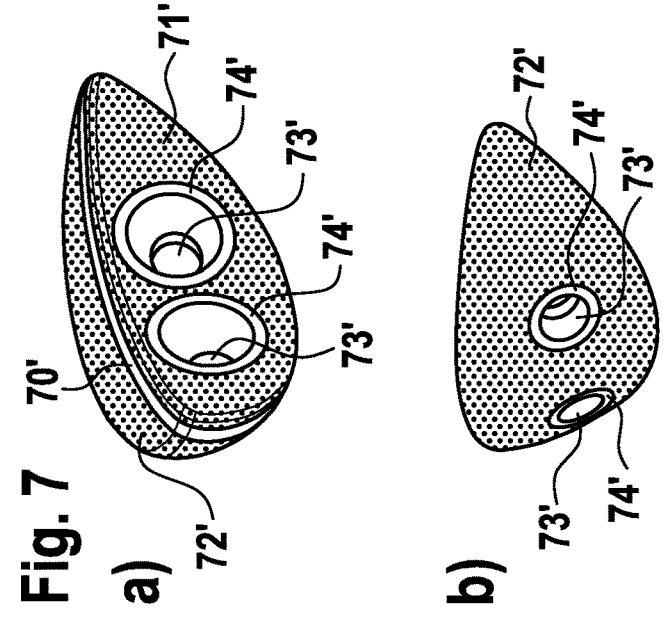
FIGS. 7a, b are detail views of the segmental augment device.

A second embodiment of a bone implant used for an endoprosthesis is shown in FIG. 6*a*, *b*. It comprises an acetabular cup 6 for the acetabular portion of hip endoprosthesis. The acetabular cup 6 is made of solid biocompatible material like in the first embodiment. However, it differs in respect to the bone implant 7'. Similar components configured for the same or similar task are denoted by a corresponding reference numeral. In the second embodiment the bone implant 7' is a segment augment shaped like a segment of a sphere. Similar to the plate augment of the first embodiment, it comprises an inner wall 70' and porous structure 71', 72' on either side thereof. More than one of the bone implants 7' may be used with and affixed to the acetabular cup 6, however for sake of simplicity just a single one is shown. The bone implant 7' may comprise passageways 73' being protected by internal linings 74', as explained in more detail above in respect to the first embodiment.

Figure 9:
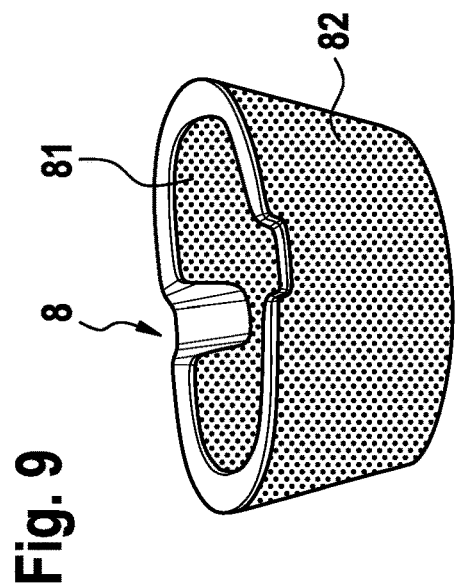
FIG. 9 shows a third embodiment of an endoprosthetic implant being shaped as tibial augment cone.
Figure 10:
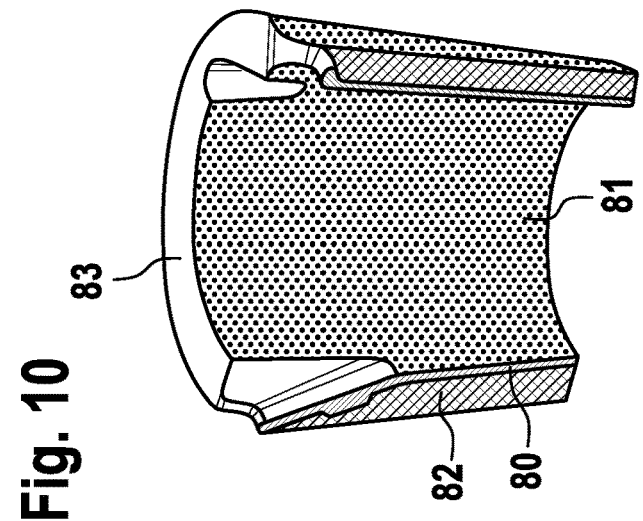
FIG. 10 is a cross-section of the tibial augment cone.

A third embodiment of a bone implant is shown in FIGS. 9 and 10. It is configured as a tibial augment cone 8 to be used for the tibial component of a knee endoprosthesis (not shown). The tibial augment cone 8 is configured to be a substitute for defective bone material at the proximal end of the tibia, filling voids caused by bone defects. Thereby a full base is formed to which the tibial component of the knee endoprosthesis can be attached. To this end the tibial augment cone 8 is manufactured using the porous structure according to the invention. A first portion 81 of the porous structure is applied on inner surface of the tibial augment cone, in order to make contact by means of bone cement (not shown) with a shaft of the tibial component passing through the interior space of the tibial augment cone 8. By virtue of the high porosity a good penetration could be achieved, thereby providing for a robust fixation. A second portion 82 of the porous structure is applied to an outer surface of the tibial augment cone 8. It is configured to promote ingrowth of bony material for long-term fixation. To avoid any unwanted migration of cement applied at the inner surface an intermediate wall 80 is provided. It acts as a bulkhead blocking an influx of cement into the porous structure 82 on the outer side. In order to avoid any spillover at a top end of the tibial augment cone 8, a top cover 83 is provided closing off the upper surface of the first and second porous structure 81, 82.

Figure 11:
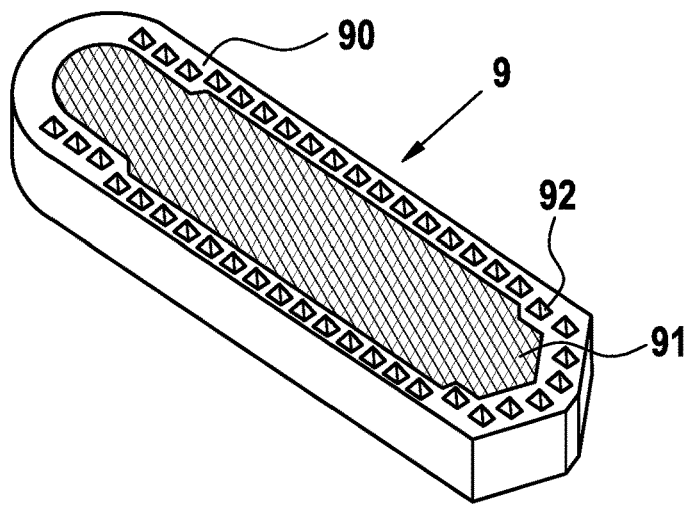
FIGS. 11a-c show variants of a fourth embodiment of an endoprosthetic implant being shaped as a spinal cage.
Figure 11:
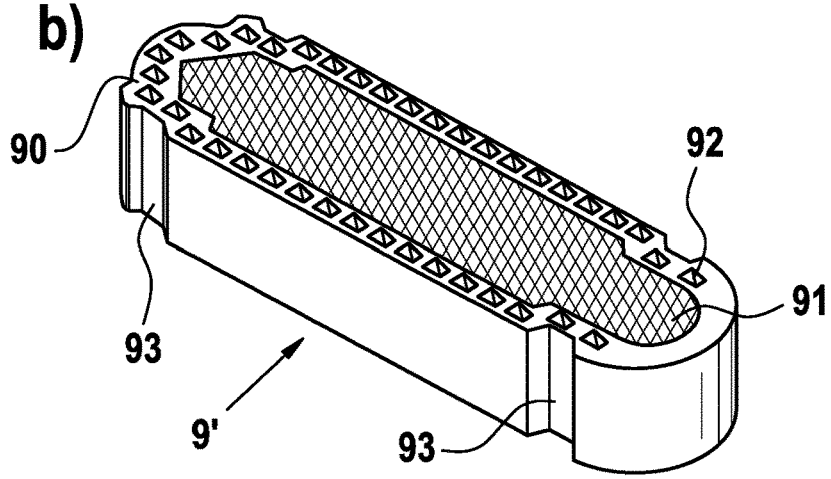
Figure 11:
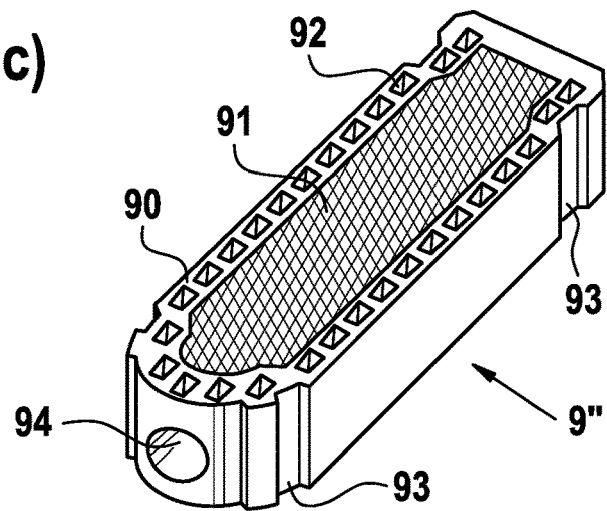

A fourth embodiment of a bone implant is shown in FIG. 11. It is configured as a spinal cage 9 to be placed into an intervertebral space for promoting fusion of two adjacent vertebrae (not shown). It acts as a substitute for an intervertebral disc and prevents collapsing of the intervertebral space in case of removal of said disc. Usually two cages 9 are placed side by side in a single intervertebral space. An inner core 91 is formed by the porous structure (in FIG. 11*a* symbolized by cross-hatching), thereby promoting bone ingrowth for improved fusioning of the two adjacent vertebra. The core 91 is surrounded by an encasement 90 made of solid material acting as a reinforcing element for providing mechanical strength to the spinal cage 9. On a top and bottom surface of the encasement 90 a plurality of teeth 92 is provided. The teeth 92 are shaped like slanted pyramids for arresting the cage into its place, thereby preventing any unwanted dislocation. A variant of a cage 9' is shown in FIG. 11*b*. It is similarly configured as the variant shown in FIG. 11*a*, however it features symmetrically arranged recesses 93 on its lateral sides acting as coupling means for an insertion instrument (not shown). Another variant of the cage 9" is shown in FIG. 11*c*. It is similar to that of FIG. 11*b*, however features in addition an attachment hole 94 at a front section of the encasement 90. The attachment hole 94 is configured with an internal thread for secure attachment to a holding instrument (not shown) having a counter-thread.

For manufacturing the bone implant 7, 8 it may be preferable to provide a three-dimensional model of the bone implant, define a body of the bone implant, define a bone contacting surface of the bone implant 7, 8 which is configured to complement a corresponding surface of the bone, wherein at least the bone contacting surface is manufactured as the porous structure. Thereby the bone implant 7, 8 may be modelled such as to match the intended implant position. This allows for a very precise manufacturing.

The method for manufacturing the bone implant that comprises a body having a porous structure and having a size and shape configured for fitment to a bone, preferably in a bone defect, may be summarized as: The method comprises manufacturing the bone implant 7, 8 by using a depositing technique to form a porous structure: forming alternating layers of basic elements shaped like tetrapods 5, arranging the tetrapods 5 in each layer in essentially parallel orientation, rotating the tetrapods 5 in every other layer with respect to the tetrapods 5 of a preceding layer, forming regularly arranged elementary cells 4 whose interior spaces form interconnected pores, the elementary cells 4 being defined by basic elements arranged in layers.

The invention claimed is:

1. A bone implant comprising:
a body having a porous structure and having a size and shape configured for fitting to a bone,
wherein the porous structure is comprised of regularly arranged elementary cells having interior spaces that form interconnected pores, the elementary cells are formed by basic elements arranged in layers, and the basic elements are shaped as tetrapods, the tetrapods in each layer being arranged in parallel orientation,
wherein the tetrapods in every other layer are rotated with respect to the tetrapods of a preceding layer,
wherein the porous structure is different from a diamond configuration.

2. The bone implant of claim 1,
wherein within a layer, three adjacent tetrapods connect with each other at a node point, node points connecting adjacent tetrapods define a base plane of the layer, and a fourth leg of each of the three adjacent tetrapods is oriented perpendicular to the base plane.

3. The bone implant of claim 2,
wherein node points of the layer are each positioned directly underneath a corresponding fourth leg of tetrapods of an adjacent upper layer such that the corresponding fourth leg is spaced from the node point directly underneath.

4. The bone implant of claim 2,
wherein legs of the tetrapods are oriented perpendicular or oblique but not parallel to the base plane.

5. The bone implant of claim 2,
wherein an angle between legs connecting at a node point and the base plane is more than 20°.

6. The bone implant of claim 2,
wherein the fourth leg is shorter than the other legs.

7. The bone implant of claim 1,
wherein the tetrapods are made in place through deposition and solidification.

8. The bone implant of claim 1,
wherein the tetrapods are formed by an Electron Beam Melting (EBM) or a Selective Laser Melting (SLM) process.

9. The bone implant of claim 1,
wherein the porous structure is made of a biocompatible material selected from a group consisting of titanium alloys, pure titanium, cobalt chromium, tantalum, stainless steel, and zirconium.

10. The bone implant of claim 9,
wherein the material is pure titanium or a titanium alloy.

11. The bone implant of claim 1,
wherein the porous structure includes a PVD coating.

12. The bone implant of claim 1,
wherein the porous structure includes a coating of calcium phosphate.

13. The bone implant of claim 11,
wherein a thickness of the coating is between 1 µm and 10 µm.

14. The bone implant of claim 1,
wherein the porous structure is attached to a solid body structure.

15. The bone implant of claim 1,
wherein the shape and size are configured to be usable for an acetabular or humeral cup or a bone augment device.

16. The bone implant of claim 1,
wherein the body is configured for fitting a bone defect.

17. The bone implant of claim 5,
wherein the angle is from 25° to 35°.

18. The bone implant of claim 1,
wherein the layers are in an alternating arrangement having rotated and non-rotated tetrapods.

19. The bone implant of claim 7,
wherein the tetrapods are made in successive layers.

20. The bone implant of claim 10,
wherein the material is titanium grade 2 or Ti6Al4V.

21. The bone implant of claim 11,
wherein the PVD coating is selected from a group consisting of niobium, tantalum, zirconium, and oxides thereof.

22. The bone implant of claim 13,
wherein the thickness of the coating is less than 7 µm.

23. The bone implant of claim 14,
wherein the porous structure is attached as a unitary structure.

24. The bone implant of claim 15,
wherein the shape and size are configured to be usable for an acetabular, humeral, femoral, or tibial augment or a cage.

25. The bone implant of claim 15,
wherein the shape and size are configured to be usable for an intervertebral cage.

26. An endoprosthetic implant comprising:
a body made of a solid material and a bone contacting portion made of a porous structure,
wherein the porous structure is comprised of regularly arranged elementary cells having interior spaces that form interconnected pores, and the elementary cells are formed by basic elements arranged in layers,
wherein the basic elements are shaped as tetrapods, the tetrapods in each layer being arranged in parallel orientation,
wherein the tetrapods in every other layer are rotated with respect to the tetrapods of a preceding layer,
wherein the porous structure is different from a diamond configuration.

27. The endoprosthetic implant of claim 26,
wherein the body is a component of an articulated joint.

28. The endoprosthetic implant of claim 26,
wherein the body is a bulkhead element dividing the porous structure into distinct sections.

29. The endoprosthetic implant of claim 26,
wherein the body is a reinforcing element.

30. The endoprosthetic implant of claim 26,
wherein the body forms a spinal cage and is configured to surround a core made of the porous structure.

31. The endoprosthetic implant of claim 27,
wherein the body is a component of a cup.

32. The endoprosthetic implant of claim 28,
wherein the bulkhead element is configured to block cement from flowing across.

33. A method for manufacturing a bone implant that comprises a body having a porous structure and having a size and shape configured for fitting to a bone, wherein the method comprises manufacturing the bone implant by using a depositing technique to:
form alternating layers of basic elements shaped as tetrapods,
arrange the tetrapods in each layer in parallel orientation,
rotate the tetrapods in every other layer with respect to tetrapods of a preceding layer, and
form regularly arranged elementary cells having interior spaces that form interconnected pores, the elementary cells being defined by the basic elements arranged in layers,
wherein the porous structure is different from a diamond configuration.

34. The method of claim 33, further comprising:
providing a three-dimensional model of the bone implant,
defining a body of the bone implant, and
defining a bone contacting surface of the bone implant which is configured to complement a corresponding surface of the bone, wherein at least the bone contacting surface is manufactured as the porous structure.

35. The method of claim 33, further comprising
depositing a coating on the porous structure by a Physical Vapor Deposition (PVD) process.

36. The method of claim 33, further comprising
depositing a CaP coating on the porous structure.

37. The method of claim 35, further comprising using tantalum for the coating.

\* \* \* \* \*